United States Patent [19]

Koga et al.

[11] Patent Number: 5,122,752
[45] Date of Patent: Jun. 16, 1992

[54] METHOD OF AND APPARATUS FOR ANALYZING GRANULAR MATERIALS

[75] Inventors: Masataka Koga; Tsuyoshi Nishitarumizu, both of Katsuta; Tetsuya Matsui; Kenji Yokose, both of Hitachi; Masaharu Sakagami, Katsuta; Takehiko Kitamori, Ushiku, all of Japan

[73] Assignee: Hitachi, Ltd., Tokyo, Japan

[21] Appl. No.: 575,422

[22] Filed: Aug. 30, 1990

[30] Foreign Application Priority Data

Sep. 16, 1989 [JP] Japan .................................. 1-240316

[51] Int. Cl.[5] .................................................. B01D 49/00
[52] U.S. Cl. ...................................... 324/464; 250/283; 210/96.1
[58] Field of Search .................. 324/459, 404, 71.4, 324/71.1; 356/317, 318, 432; 250/283; 55/4, 102; 340/618; 210/96.1, 746

[56] References Cited

U.S. PATENT DOCUMENTS

| | | | |
|---|---|---|---|
| 2,387,550 | 10/1945 | Windler | 250/283 |
| 2,950,387 | 8/1960 | Brubaker | 55/102 |
| 2,959,677 | 11/1960 | Robinson et al. | 250/423 P |
| 3,859,526 | 1/1975 | Hirschfield | 324/71.4 |
| 3,948,625 | 4/1976 | Schultz | 55/102 |
| 4,160,161 | 7/1979 | Horton | 250/283 |
| 4,259,573 | 3/1981 | Prober et al. | 250/283 |
| 4,320,394 | 3/1982 | John, Jr. | 340/618 |
| 4,574,004 | 2/1986 | Schmidt-Off et al. | 324/469 |
| 4,713,548 | 12/1987 | Kim et al. | 250/283 |
| 4,996,422 | 2/1991 | Mitsui et al. | 250/283 |

Primary Examiner—Kenneth A. Wieder
Assistant Examiner—Maura K. Regan
Attorney, Agent, or Firm—Antonelli, Terry, Stout & Kraus

[57] ABSTRACT

A method of and an apparatus for analyzing a granular material contained in a sample of a medium such as water produced by an ultra-pure water producing apparatus includes the steps of adding energy to granular materials contained in a sample which is mixed with the medium, wherein the energy is set to be lower than the breakdown threshold of the medium and to be higher than the breakdown threshold of the granular materials, detecting ions which are generated with the breakdown of the granular materials by using a pair of positive and negative electrodes; and analyzing characteristics of the granular materials based on the ions.

19 Claims, 7 Drawing Sheets

METHOD OF AND APPARATUS FOR ANALYZING GRANULAR MATERIALS

BACKGROUND OF THE INVENTION

The present invention relates to an analytical method and apparatus which are well suited for the multifarious analyses of a granular material, such as impurities, contained in a sample, and an ultra-pure water producing and managing system which utilizes them.

There have heretofore been proposed various techniques for detecting and measuring granular materials (fine grains) which remain in ultra-pure water and various medical fluids for use in a multiplicity of fields such as semiconductors, medicines and biochemistry, and in the air and various other gases within clean rooms.

One prior-art example which is well known is a scattered light system. This system detects a granular material in such a way that a sample is irradiated with a laser beam, and the scattered light from grains is detected. In such a system, since scattered light from a medium forms the background, a large number of noise factors are involved in the measurement, and the measurement of ultramicrons is difficult.

Therefore, a variety of grain measuring systems to replace this example have been proposed.

For example, prior-art techniques disclosed in the official gazettes of Japanese Patent Laid-open No. 50-91390 (1975) and No. 52-28389 (1977) detect the concentration of a granular material in such a way that corona discharge is induced in a sample gas, thereby electrifying grains contained in the sample, and an ionic current the sense of which is reverse to the moving sense of the charged grains is detected.

Further, the inventors have recently developed a grain measuring method utilizing an photo-acoustic effect, as stated in JAPANESE JOURNAL OF APPLIED PHYSICS, Vol. 27 NO. Jun. 6, 1988, pp. L983-L985. In the grain measuring method which utilizes the photo-acoustic effect, only grains in a sample are broken down by irradiating the grains with a laser beam or the like, and the acoustic wave of a plasma generated on this occasion is detected by a piezoelectric transducer, whereby the grain sizes and numerical density of the granular material are measured on the basis of the magnitude and number of detection signals.

As another prior-art technique, an improvement on the scattered light detecting system is disclosed in the official gazette of Japanese Patent Laid-open No. 63-142234 (1988).

Among the prior-art techniques mentioned above, the system wherein the grains in the sample are electrified by corona discharge is restricted to the measurement of grains in gases, and it is not suitable for measurements concerning granular materials contained in liquid samples.

On the other hand, the photo-acoustic system already developed by the inventors gives rise to the breakdown of only the grains of the sample and, in turn, the plasma phenomenon by virtue of the light irradiation. Note should be taken of the fact that the grains in the sample exhibit a breakdown threshold value smaller than that of the medium. It is appreciated as having the advantages that the accuracy of the measurement is enhanced and that the grains can be measured irrespective of whether the sample is a gas or a liquid.

With this system based on the photo-acoustic effect, however, the internal structure of a sample cell becomes complicated because the piezoelectric transducer for converting the acoustic wave into an electrical signal is built in the cell. In addition, since a dispersion is involved in the characteristics of the individual piezoelectric transducers, means for correcting the dispersion is needed. Besides, the irradiation of the piezoelectric transducer with the laser beam causes of the degradation of the characteristics, so that a consideration therefor is needed.

SUMMARY OF THE INVENTION

The present invention has been made in view of the aforementioned problems and has for its object to provide an analytical method and apparatus in which, irrespective of whether a sample is a liquid or a gas, a granular material (fine grains) coexisting with or remaining in the sample can have the size, numerical density, concentration etc. thereof measured with a very high accuracy, which can simplify the structure of a sample cell as compared with the photo-acoustic effect system, and which can simplify a measurement mechanism without involving the dispersion of characteristics as in piezoelectric transducers, and also an ultra-pure water system which utilizes them.

The object is accomplished as follows:

As the fundamental expedient for solving the problems (which is the first expedient for solving the problems), there is proposed a method of analyzing a granular material in a sample, comprising:

applying energy to the sample at a level which is lower than a breakdown threshold value of a medium of the sample and which is higher than a breakdown threshold value of the granular material contained in the sample, thereby to selectively break down only the granular material;

arranging a pair of electrodes with the sample held therebetween, thereby to attract cations of a plasma induced by the breakdown to a negative one of said electrodes and to attract anions and electrons to a positive one of said electrodes; and detecting a current, voltage, resistance or capacitance across the electrodes.

Here, as the aspect of the analysis, it is mentioned that the size, numerical density, concentration etc. of the granular material are measured on the basis of any of the current, voltage, resistance and capacitance across the electrodes.

In addition, as energy application means for giving rise to such selective breakdown, means for projecting a laser beam is proposed by way of example. More specifically, the output density of the laser beam is set to be lower than the breakdown threshold value of the medium in the sample and higher than the breakdown threshold value of the granular material.

Further, as the second expedient for solving the problems, there is proposed a method in which, besides the analytical method of the first expedient for solving the problems, light of the plasma induced by the breakdown is spectroscopically analyzed to detect the light emission spectrum thereof, and components of the granular material are analyzed on the basis of the spectral detection signal.

The third expedient for solving the problems concerns an inventive apparatus for use in the analytical method of the first expedient for solving the problems and comprises:

a cell in which the sample is received;

laser beam projection means for irradiating the sample in the cell with a laser beam, the means having a function of setting the output density of the laser beam so as to be lower than the breakdown threshold value of the medium of the sample and higher than the breakdown threshold value of the granular material contained in the sample;

a pair of electrodes which are arranged inside or outside the cell while holding the sample therebetween;

means for applying a constant voltage across the electrodes;

means for detecting a current, voltage, resistance or capacitance across the electrodes when only the granular material in the sample has been broken down; and means for computing at least one of the size, numerical density and granular concentration of the granular material in the sample on the basis of the detected data.

The fourth expedient for solving the problems concerns an inventive apparatus for use in the analytical method of the second expedient for solving the problems and comprises besides the constituents mentioned in the third expedient for solving the problems:

means for spectroscopically analyzing a plasma developed when the granular material has been broken down and detecting the light emission spectrum thereof; and means for storing relations between components of granular materials and light emission spectra as retrieval data beforehand, and analyzing components of the granular material on the basis of detection signals of the detected light emission spectrum.

The fifth expedient for solving the problems concerns the inventive application of the granular material analyzing method and apparatus to an ultra-pure water producing and managing system and comprises:

an ultra-pure water producing apparatus which is constructed of a plurality of devices;

a cell into which at least part of the ultra-pure water produced by the ultra-pure water producing apparatus is introduced as a sample;

laser beam projection means for irradiating the sample in the cell with a laser beam, the means being capable of setting the output density of the laser beam so as to be lower than the breakdown threshold values of water and air and higher than the breakdown threshold value of the granular material contained in the sample;

a pair of electrodes which are arranged inside or outside the cell while holding the sample therebetween;

means for applying a constant voltage across the electrodes;

means for detecting a current, voltage, resistance or capacitance across the electrodes when the granular material in the sample has been broken down;

means for computing at least one of the size, numerical density and granular concentration of the granular material in the sample on the basis of the detected data;

means for determining the quality of the produced ultra-pure water from the computed data; and means for shutting off feed of the sample from the ultra-pure water producing apparatus to a user and issuing an alarm to that effect when the quality of the sample has been determined to be inferior.

DETAILED DESCRIPTION OF THE PREFERRED EMBODIMENTS

As also stated on the photo-acoustic effect system in the foregoing literature (JAPANESE JOURNAL OF APPLIED PHYSICS) and Japanese Patent Application No. 85094/1988, the inventors have found out that the breakdown threshold value of grains (here, polystyrene grains are exemplified) is lower than those of gases, such as air, and liquids, such as water. More specifically, as breakdown threshold values, it has been experimentally determined that air exhibits $5 \times 10^{12}$ W/cm$^2$, that the water exhibits $3 \times 10^{11}$ W/cm$^2$ and that polystyrene grains exhibit $4 \times 10^{10}$ W/cm$^2$. By utilizing such threshold value characteristics, accordingly, the energy to be applied to the sample is set at a level which is lower than the breakdown threshold value of the medium of the sample and which is higher than the breakdown threshold value of the granular material contained in the sample, as in the first expedient for solving the problems Then, only the granular material in the sample is selectively broken down, and plasma is developed.

Subsequently, the cations generated by the plasma are attracted to the negative electrode, and the electrons and the anions to the positive electrode, so that the current, voltage, resistance and capacitance across the electrodes undergo changes. When any of the changes is detected, the quantity of electric charges caused by the breakdown is found, and in turn, analysis of the granular material before the occurrence of the breakdown becomes possible As the analysis on this occasion, the size of the granular material can be found from the magnitude of the detected signal in, for example, a case where the sample is ultra-pure water and where the impurities (granular material) are rarely existent. A measurement accuracy on this occasion can be heightened on the ground that, since the breakdown of the medium does not occur, noise factors can be excluded.

Here, let's consider signals which are generated when grains having a diameter of 0.01 $\mu$m are broken down. Assuming that the specific gravity of the grains is "1", the weight of one grain is $0.524 \times 10^{-19}$ gr. In the case where the principal component of the grains is carbon, the number of atoms in the single grain is $0.263 \times 10^5$. If all the atoms are ionized into monovalent ions the, electric charge based on electrons or cations becomes $0.421 \times 10^{-14}$ C, and the crest value of a voltage pulse becomes 0.421 mV, which is sufficiently greater as compared with noise usually encountered. As a result, it is possible to measure fine grains of 0.01 $\mu$m.

Moreover, when the detection signals are counted, the numerical density of the granular material in the sample can be measured, or when the average value of the detection signals is taken, the concentration of the granular material can be found.

Further, in the case where the sample is a liquid, the energy for breaking down the granular material is previously set at a level which is lower than not only the breakdown threshold value of the liquid sample, but also that of air bubbles (the air) which appear in the sample. Thus, a situation in which the air bubbles are erroneously broken down in prevented, so that the accuracy of detection can be heightened still more.

Meanwhile, when the electrodes for use in this expedient for solving the problems are made of a material of high electric conductivity, the problem of the dispersion of characteristics dependent upon the material of the electrodes does not arise, and a stable detection accuracy can be maintained by controlling the electrode configuration, the interelectrode distance and the applied voltage.

Next, according to the second expedient for solving the problems, the light of the plasma induced by the breakdown is spectroscopically analyzed, and the light emission spectrum of the plasma is detected. In the light emission spectrum in this case, peak wavelength regions differ depending upon the components of the granular material. Therefore, the analysis of the components of the granular material is determined by finding the peak wavelength regions.

When, in the case of analyzing the components of the granular material on the basis of the light emission spectrum in this manner, a laser beam is employed as the means for irradiating the sample, the wavelength of the laser beam is set outside the range of the wavelengths of the light emission spectrum to be developed by the breakdown, whereby the laser beam is readily distinguished, and the accuracy of the analysis can be enhanced.

Figure 1:
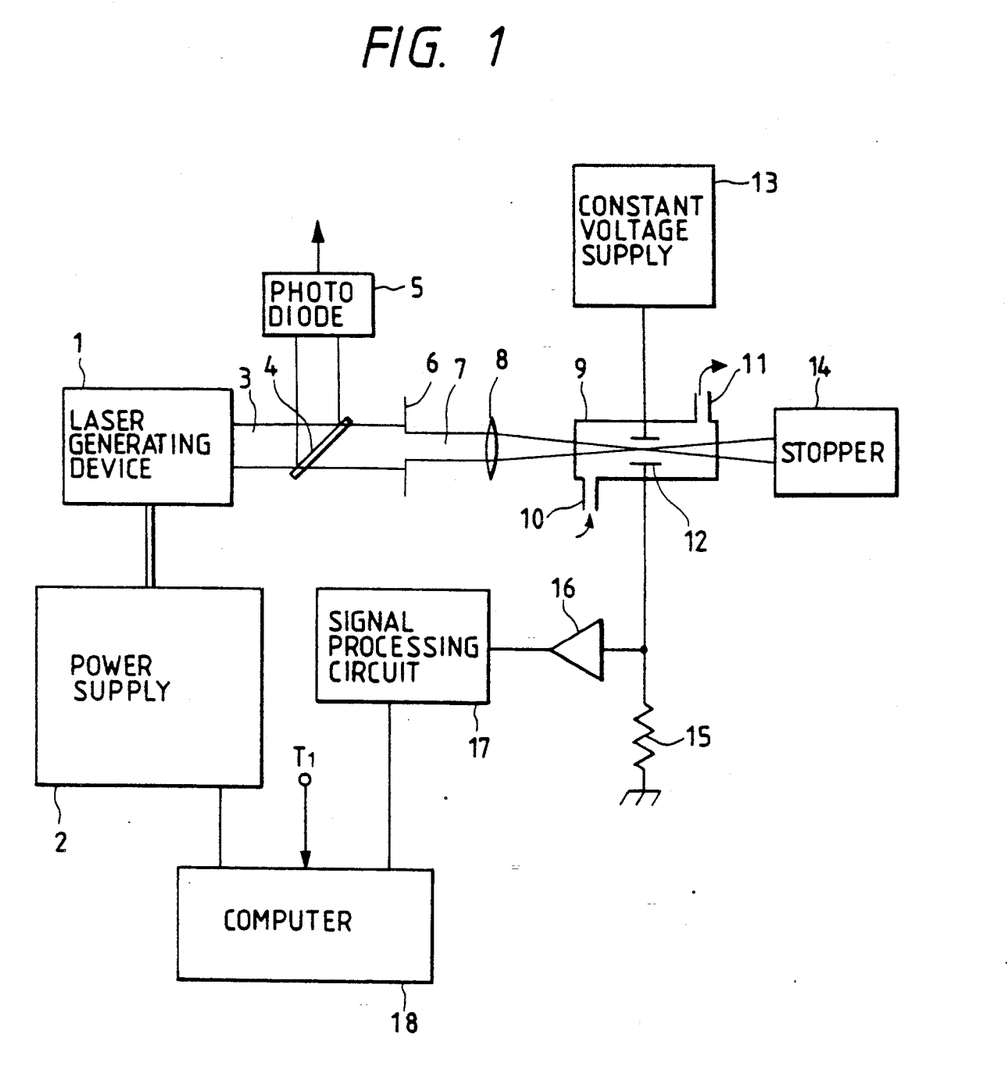
FIG. 1 is a block diagram showing the first embodiment of the present invention.
Figure 7:
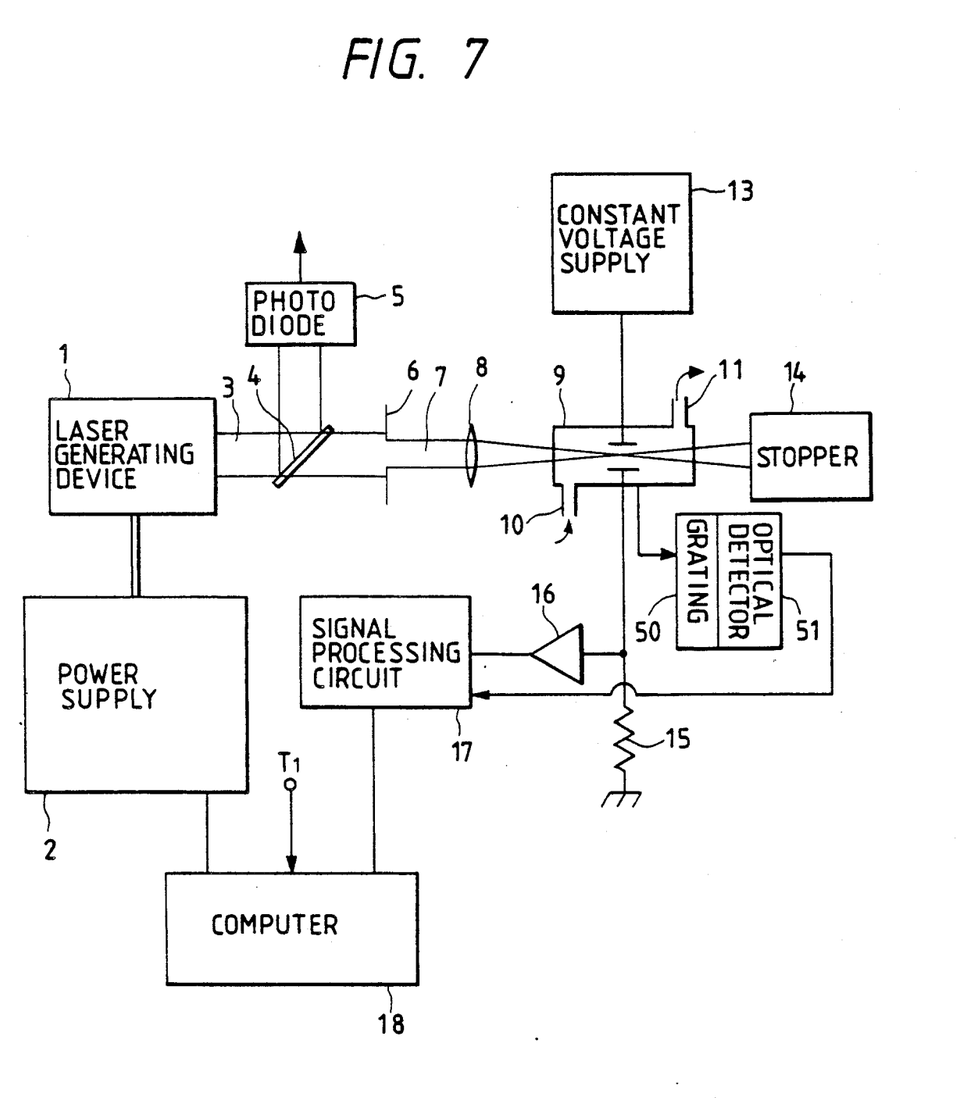
FIG. 7 is a block diagram showing the second embodiment of the present invention.
Figure 8:
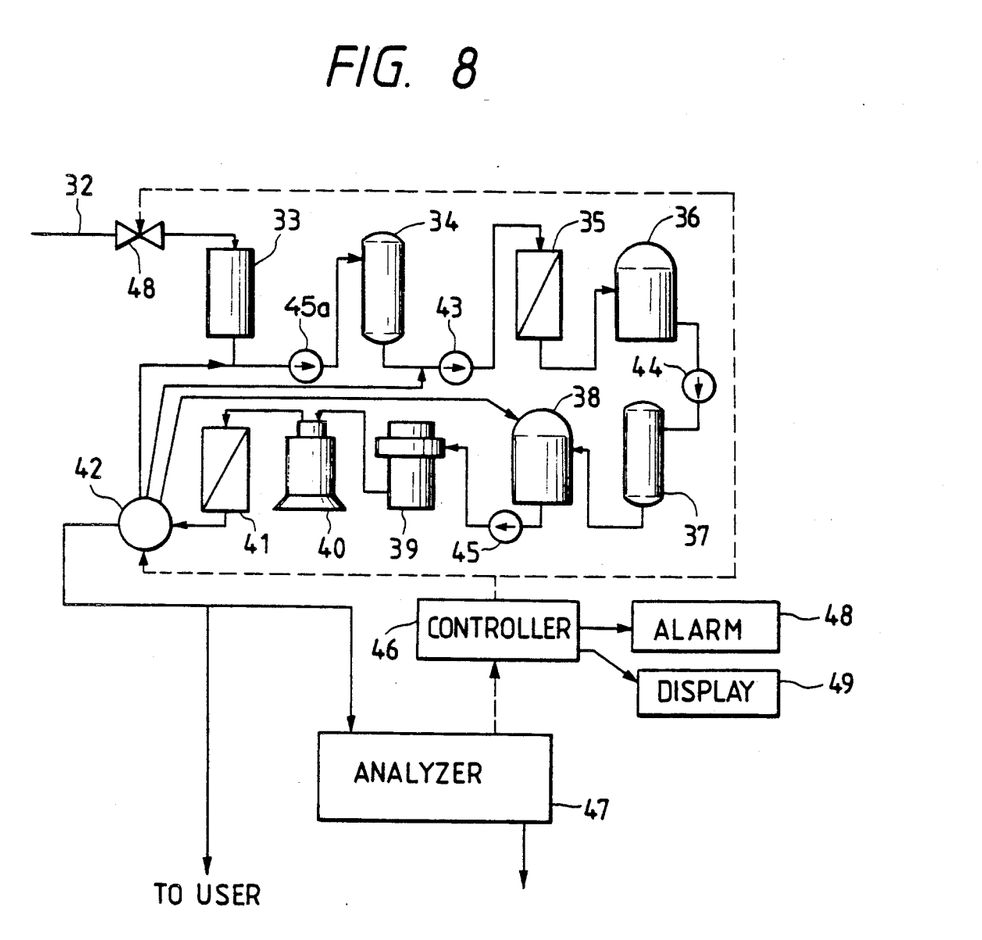
FIG. 8 is a constructional diagram showing the application system of an ultra-pure water producing and managing system of the present invention.

Incidentally, the third expedient for solving the problems corresponds to the embodiment in FIG. 1, the fourth expedient for solving the problems corresponds to the embodiment in FIG. 7, and the fifth and sixth expedients for solving the problems correspond to the embodiment in FIG. 8. Therefore, the operation of these expedients shall be described in detail in the description of the embodiments.

The embodiments of the present invention will be described with reference to the drawings.

FIG. 1 is a system block diagram showing the first embodiment of the present invention, and FIG. 2 thru FIG. 5(D) are explanatory diagrams showing the operating status of the embodiment.

Referring to FIG. 1, numeral 1 designates an Nd:YAG (yttrium-aluminum-garnet) laser, which generates a laser beam 3 under the control of a power supply 2. The Nd:YAG laser 1 oscillates at a wavelength of 1064 nm. The laser beam 3 to be used may be the fundamental wave of 1064 nm. Alternatively, it may well be the second harmonic of 532 nm, the third higher harmonic of 355 nm, or the fourth harmonic of 266 nm. The laser beam 3 is partly reflected by a quartz plate 4 or the like and has its optical output monitored using a photodiode 5 or the like.

The part of the laser beam 3 transmitted through the quartz plate 4 has its beam diameter refined to a fixed value by an aperture 6, and the laser beam 7 passed through the aperture 6 is focused inside a cell 9 by a lens 8. A sample is introduced into the cell 9 through an inlet 10, and is discharged through an outlet 11.

The cell 9 in this embodiment has the function of automatically changing samples. The embodiment has a structure in which the laser beam passed through the cell 9 is absorbed by a stopper 14 so as not to leak to the exterior.

A pair of electrodes 12 are disposed in the cell 9. Thus, cations and electrons as well as anions which are created by the phenomenon of laser breakdown are separated and are collected at the electrode elements (negative electrode and positive electrode) by an electric field which is established across the electrodes 12.

One of the electrodes 12 has a constant voltage applied thereto by a constant voltage supply 13, while the other is grounded through a resistor 15. Electric signals generated when the electric charges are collected at the electrodes 12, are amplified by a preamplifier 16 and then applied to a signal processing circuit 17. Further, the signals are computed in terms of grain size distribution and grain number density in the sample by a computer 18.

In addition, the computer 18 functions to control the power of the laser power supply 2 and to receive detection data on the optical output of the laser beam 3 from the photodiode 5. Thus, in a case where the optical output fluctuates, the computer 18 recognizes the fluctuation on the basis of the detection data and corrects its output signal by storing the relations between the optical outputs and signal intensities beforehand.

Figure 2:
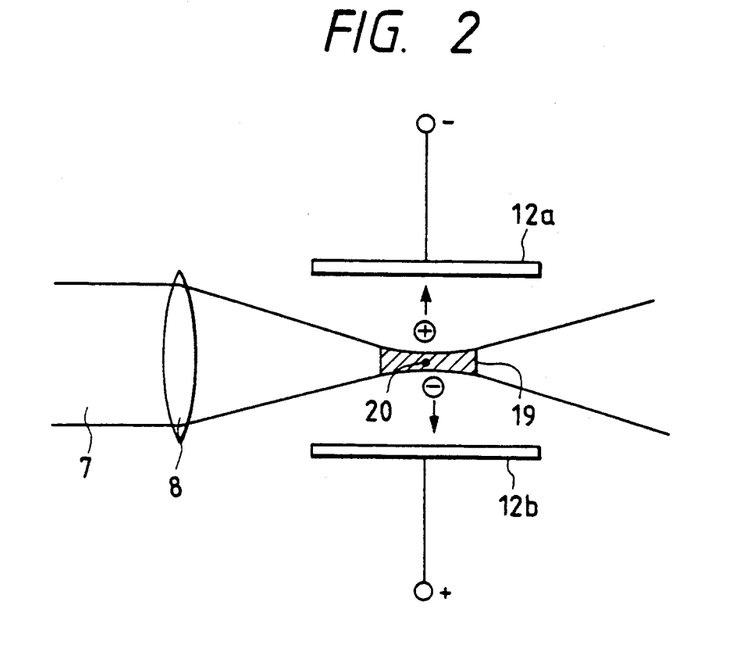
FIG. 2 is a explanatory view showing the operating principle of the first embodiment.

Here, the creation and collection of the electric charges across the electrodes 12 will be described in detail with reference to FIG. 2.

The laser beam, 7 which is a collimated light beam is focused on a focal position within the cell 9 by the lens 8. In FIG. 2, a focused portion is exaggeratedly shown. A hatched part in the focused portion is a region which is called a "beam waist" 19 and in which grains contained in the sample are broken down.

The optical density in the beam waist 19 is set at a threshold level which does not induce breakdown for a sample medium (for example, water) or air bubbles (the air), but which induces breakdown for the granular material (impurities) in the sample.

Thus, when a grain 20 exists in the beam waist 19, upon the irradiation thereof with the laser beam 7 the grain is broken down to turn into a plasma.

The electrodes 12 consist of a negative electrode 12a and a positive electrode 12b. The cations created by the plasma are attracted to the negative electrode 12a, while the electrons or the anions are attracted to the positive electrode 12b.

In this embodiment, the laser 1 is energized in a pulsed manner with a fixed period, and the volume of the beam waist 19 is determined by the energy for pulsedly lighting up the laser 1, the diameter of the laser beam 7, and the focal distance of the lens 8. The sample is kept flowing through the cell 9, and the flow velocity thereof is set and maintained so that the sample part in the beam waist 19 may be different with every lasing pulse.

When, under the above conditions, the ratio between the number of the laser shots and the number of the electrical signals generated across the electrodes 12 in the cell 9 by the breakdown is evaluated, the numerical density of the grains in the sample is obtained. Besides, the sizes of the grains are obtained from the magnitudes of the individual electrical signals Incidentally, the measurements of the numerical density of the grains and the sizes of the grains in this case are premised on the sample in which the granular material is rarely existent.

Several measuring methods and electrical signals obtained using them will be described with reference to FIGS. 3(A)-3(D).

Figure 3A:
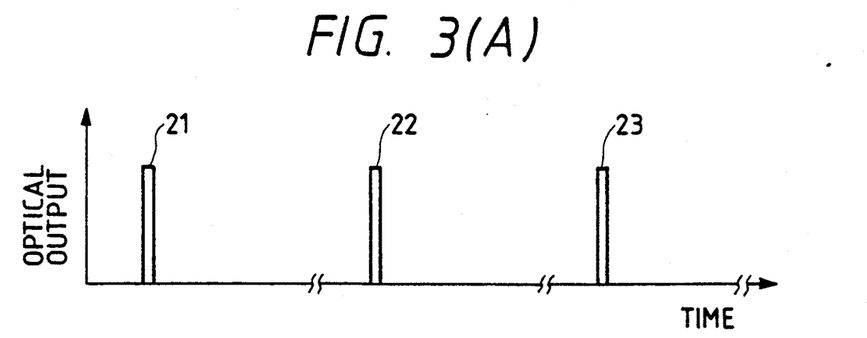
FIGS. 3(A)–3(D) are explanatory diagrams showing the signal waveform of the first embodiment.
Figure 3B:
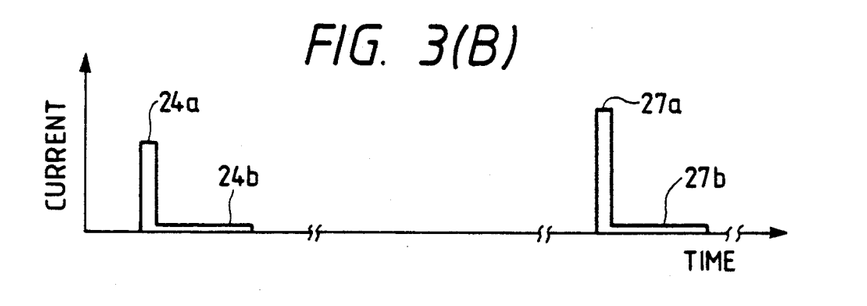

FIG. 3(A) shows the waveform of the optical output of the laser. As practicable conditions, a wavelength of 532 nm is employed, the energy of each of the laser shots 21, 22 and 23 is set at 30 mJ, the duration of one shot is set at 10 nsec, and the shots are repeated with a repetition rate of 20 Hz. When the grain 20 exists in the beam waist 19 during the laser shot 21, a current signal indicated at 24a and 24b is produced, as shown in FIG. 3(B), by the plasma which is induced by the selective breakdown of the granular material. Current components in this case are of two sorts; the current 24a based on the electrons and the current 24b based on the ions. In general, the mobilities of the electrons and the ions exhibit a difference of 3 orders approximately, so that if the current 24a based on the electrons has a duration in the order of $\mu$sec., the current 24b based on the ions has a duration in the order of msec. During the second shot 22, no grain exists in the beam waist 19, and no signal concerning the breakdown is generate. Greater currents 27a, 27b are produced during the third shot 23, and they signify detection of the grain of larger size.

In this way, the size of the granular material can be determined from the magnitude of the current signal (electrical signal), and the grain number density can be determined from the number of electrical signals.

In evaluating the grain number density, it is convenient to neglect the currents 24b, 27b based on the ions and top process the signals with note taken of only the pulses of the currents 24a, 27a based on the electrons.

Figure 3C:
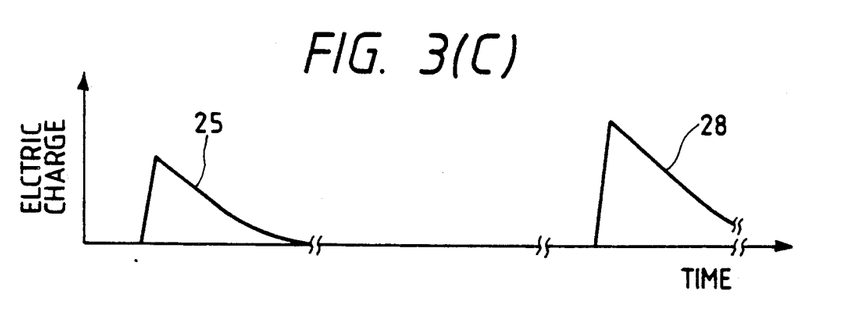

FIG. 3(C) shows the electrical charges collected at the electrodes 12. The electrodes 12 function as a capacitor, and can store the charges. The charges stored on the electrodes 12 are discharged through the resistor 15 which provide a time constant such that the charges decrease exponentially as indicated at numeral 25 and may return to zero by the next shot 22. When the grain exists during the shot 23, an electrical charge pulse 28 is produced.

Figure 3D:
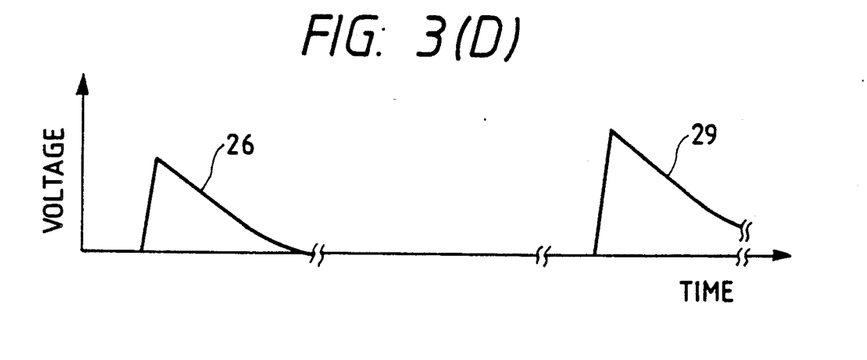

FIG. 3(D) shows the waveforms of voltage pulses 26, 29 which have been generated in the electrodes 12 forming the capacitance by the electrical charges illustrated in FIG. 3(C). The crest value of the voltage pulse 26 is proportional to the integral value of the current 24a based on the electrons, namely, the total charges of the electrons. The same holds true also of the voltage pulse 29 and the current 27a.

Figure 4:
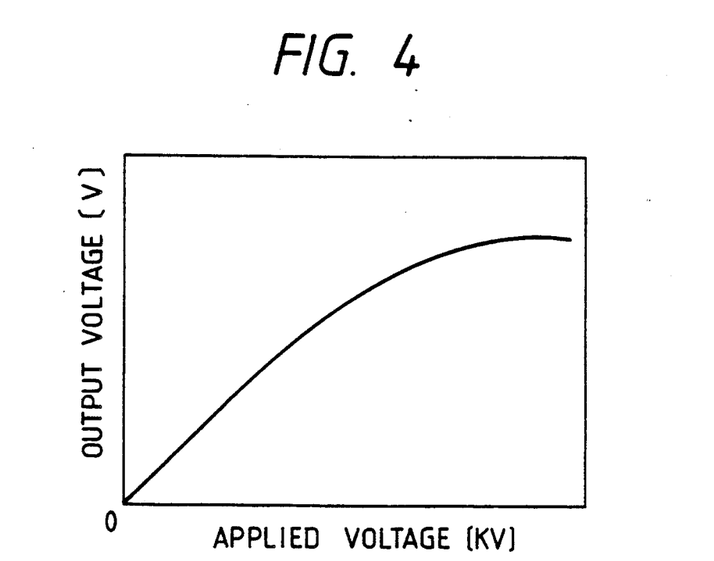
FIG. 4 is an explanatory diagram showing an output voltage characteristics exhibited when a voltage is applied across the electrodes of the first embodiment.

FIG. 4 shows the relationship between the applied voltage and the output voltage (=the crest value of the voltage pulse) across the electrodes 12 in the method of detecting the voltage pulses 26, 29.

As illustrated in the figure, by raising the applied voltage, the electrons have their moving speeds increased to decrease the probability that they recombine with the cations and to increase the proportion of electrons which reach the electrode 12, so that the output voltage is also increased. When the recombination has become negligible, the output voltage is saturated.

Thus, according to this embodiment, the grains having diameters of 0.01 $\mu$m are permitted to be caught and to be measured or counted. By the way, the ground on which the grain diameter of 0.01 $\mu$m is caught has been stated in the chapter of the "Operations" of the invention, which shall therefore be referred to.

Figure 5A:
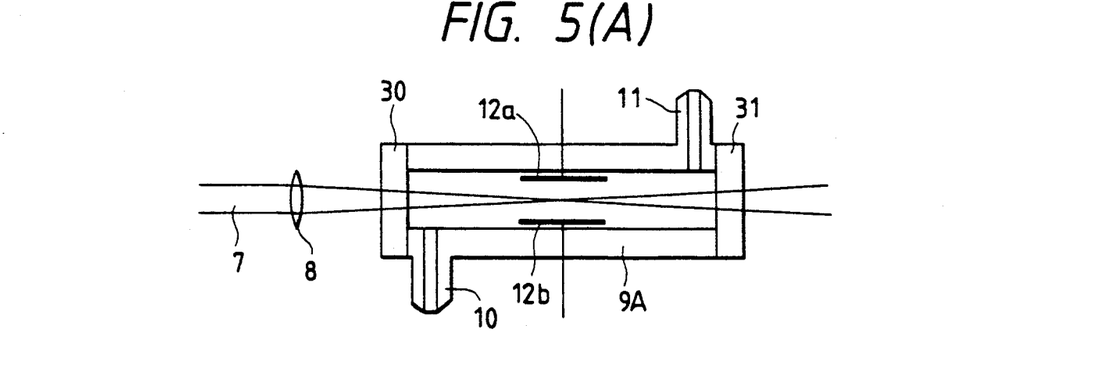
FIGS. 5(A) and 5(D) are explanatory views showing the arrangement of the electrodes of the first embodiment.
Figure 5B:
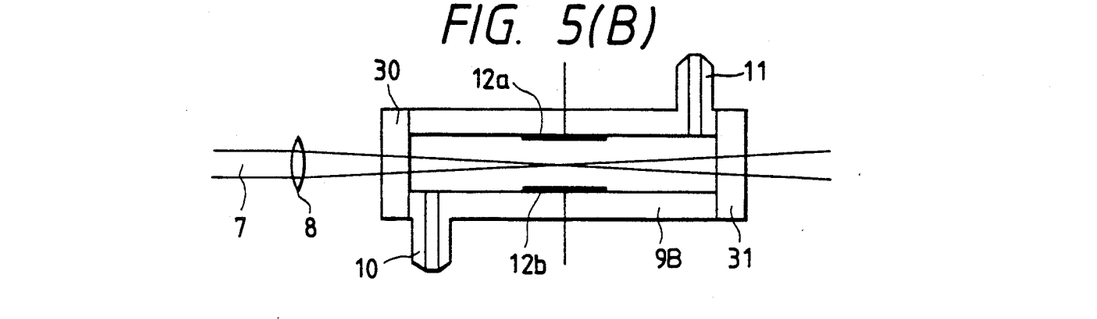
Figure 5C:
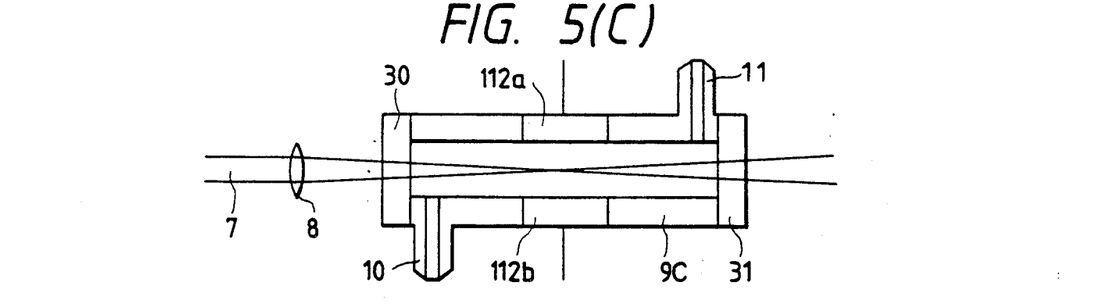
Figure 5D:
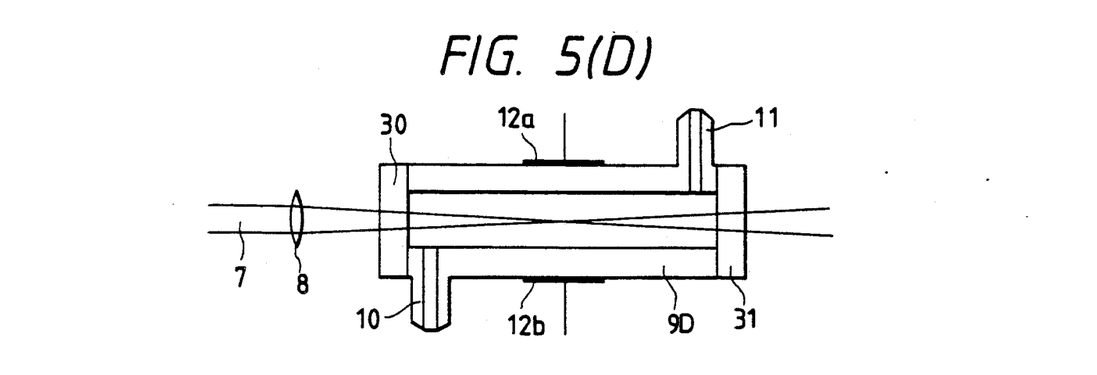

FIGS. 5(A)-5(D) show alternative structures 9A-9D of the cell 9 for use in this embodiment. Each of the cells 9A-9D is furnished with an entrance window 30 at one end in the lengthwise direction thereof and with an exit window 31 at the other end. After passing through the focusing lens 8, the laser beam 7 enters the cell 9 through the entrance window 30. Further, after passing through the cell 9, the laser beam 7 emerges out of the exit window 31. FIG. 5(A) illustrates an example in which the electrodes 12 (12a, 12b) are disposed within the cell 9A, FIG. 5(B) an example in which the electrodes 12a, 12b are stuck on the inner wall of the cell 9B, FIG. 5(C) an example in which parts of the cell 9C are made of the electrodes 112a, 112b, and FIG. 5(D) an example in which the electrodes 12a, 12b are stuck on the outer surface of the cell 9D.

Figure 6A:
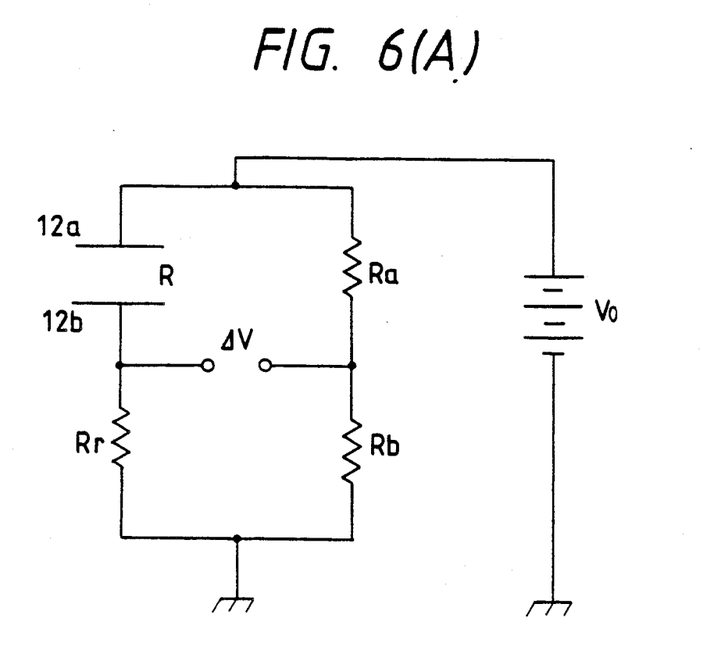
FIGS. 6(A)–6(B) are explanatory diagrams showing, different signal processing examples of the first embodiment.
Figure 6B:
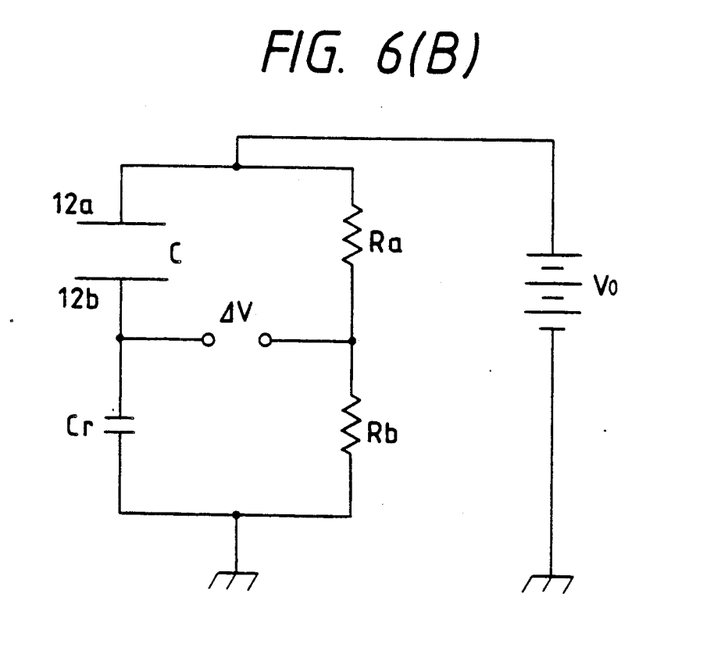

FIG. 6(A) and 6(B) exemplify different ways of picking up the detection signals across the electrodes 12 (the breakdown phenomenon of the granular material existing in the sample).

FIG. 6(A) shows an example in which, with note taken of the fact that the resistance R across the electrodes 12a, 12b changes upon the occurrence of breakdown, the granular material is measured by evaluating the change of the resistance. In this case, R denotes the resistance exhibited when breakdown is not induced, R·Rb = Rr·Ra is set beforehand so that a bridge circuit is balanced at this time (i.e., so that the intermediate voltage difference $\Delta V$ of the bridge is zero). Under the present condition, assuming that the resistance has been changed to $(1-\alpha)$R by the breakdown, $$\Delta V \approx \frac{Ra\,Rb}{(Ra + Rb)^2} \alpha V_o$$

is held, and the signal proportional to the rate $\alpha$ of change is obtained. That is, since the current shown in FIG. 3(B) is in the form of $\alpha$, information on the size of the grain is obtained by detecting $\Delta V$.

FIG. 6(B) shows a method in which, with note taken of the fact that the capacitance across the electrodes 12a, 12b changes in the presence of the electrons and the ions created by the breakdown, data on the granular material is detected by detecting the change.

In this example, a bridge which has the relationship of C·Rb = Cr·Ra before the occurrence of breakdown is set using the capacitance C of the electrodes 12a, 12b, a fixed capacitance Cr, and resistances Ra, Rb. Assuming that the capacitance of the electrodes 12a, 12b has been changed to $(1+\alpha)$C by the breakdown, $$\Delta V \approx \frac{Ra\,Rb}{(Ra + Rb)^2} \alpha V_o$$

is held. In the same manner as in FIG. 6(A), the data on the granular material is obtained by finding an intermediate voltage difference $\Delta V$.

In the embodiment thus far described, the information items of the electric charges created across the electrodes with the breakdown have been handled in pulse fashion. However, when the average current across the electrodes is measured instead of the pulse information items, the concentration of the granular material can also be determined from the average current value.

According to this embodiment, as already stated, it is possible to measure and count fine grains whose diameters are 0.01 μm or or so. In particular, it is possible to determine the grain size distribution, of the grains from the magnitudes of the pulsed electrical signals generated across the electrodes 12 by the breakdown and to know the numerical density of the grains from the rate of generation of the pulse signals. Further, it is possible to measure the concentration of the granular material on the basis of the average current value.

Moreover, when compared with the prior-art photoacoustic effect system employing a piezoelectric transducer, the embodiment has the advantage that the electrodes for detecting breakdown of the granular material avoid a dispersion in the characteristic of the detecting transducers and detect stable signals. As another advantage, the cell structure can be simplified in comparison with that of the piezoelectric transducer type.

FIG. 7 shows the second embodiment of the present invention. This embodiment is such that a grating 50 and an optical detector 51 are added to the components of the first embodiment. Besides the measurements of the grain size distribution and the grain number density, this embodiment analyzes the components of the granular material. More specifically, a light emission spectrum developed by the breakdown is detected through the grating 50 and the optical detector 51, and the detected signal is input to the computer 18 through the signal processing circuit 17. The computer 18 stores the relationships between the components of granular materials and light emission spectra as retrieval data beforehand. Thus, when supplied with the spectral detection signal, the computer 18 analyzes the components of the granular material on the basis of the peak wavelength regions of the light emission spectrum. The wavelength of the laser beam for use in the second embodiment is set outside the wavelength range of the light emission spectrum.

An ultra-pure water managing system which utilizes the analytical apparatus of the above embodiment (for measuring the granular material) will be described with reference to FIG. 8.

In FIG. 8, numeral 32 designates a raw water feed line which supplies a distilling column 33 with raw water such as city water, numeral 34 is an active carbon filtration tower which eliminates organic substances etc., numeral 35 is a reverse-osmotic module which eliminates granular materials, electrolytes etc., numeral 36 is a relay tank, numeral 37 is an ion-exchange resin tower which eliminates electrolytes etc., numeral 38 is a pure water tank which stores produced pure water, numeral 39 is an ultraviolet sterilizer which sterilizes fungi, numeral 40 is a polisher which eliminates electrolytes, and numeral 41 is an ultrafilter module which eliminates fine grains, etc. Ultra-pure water, which has a specific resistance of at least 18 KcmΩ and in which the number of fine grains of 0.05–0.1 μm is at most 50/cc., is supplied from the ultra-filter module 41 to a five-way valve 42. Numerals 43–45 and 45a indicate circulating pumps of pressure pumps.

The produced ultra-pure water is fed from the five-way valve 42 to an analyzer or impurity monitor (granular material analyzer) 47. The analyzer 47 is constructed similarly to the apparatus explained in the first or second embodiment.

More specifically, in a case where any impurity exists in the produced ultra-pure water, the analyzer 47 breaks down the impurity selectively owing to the irradiation with the laser beam, and it detects the breakdown phenomenon by means of the electrodes. Thus, when the granular material (impurity) in excess of a prescribed value has been detected in the ultra-pure water, a controller 46 determines that the operation of the ultra-pure water producing apparatus is defective and issues a stop signal. It shuts off the feed of the produced water from the ultra-pure water producing apparatus to the user of the system, and it communicates to that effect to a managerial operator through an alarm 48. Here, the alarm 48 includes aural ones such as a buzzer and visual ones such as an indicating lamp.

In this way, according to such a managing system, the feed of inferior water can be shut off when any device in the ultra-pure water producing apparatus has undergone a fault or a defective operation, whereby the reliability of the producing and managing system can be enhanced.

Incidentally, with the ultra-pure water producing and managing system, it is also possible to search for any defective device from among the constituent devices of the ultra-pure water producing apparatus by, for example, analyzing the components of the granular material on the basis of the light emission spectrum developed by the breakdown phenomenon. When the defective device is searched for in this manner and is indicated on a display 49, the operations of inspecting and repairing the apparatus are facilitated advantageously.

As described above, according to the analytical method and apparatus of the present invention, only granular material is selectively broken down, and the breakdown phenomenon is detected by electrodes. Therefore, whether a sample is a liquid or a gas, the size, numerical density, concentration etc. of the granular material (fine grains) coexisting with or remaining in the sample can be measured with a very high precision. Moreover, as compared with the photo-acoustic effect system, the method and apparatus of the invention can simplify the structure of a sample cell and can simplify a measurement mechanism without involving the dispersion of characteristics as in piezoelectric transducers.

Further, according to an ultra-pure water producing and managing system which utilizes the method and apparatus, ultra-pure water can be managed automatically and appropriately.

We claim:

1. A method of analyzing a fluid medium containing a granular material, said method comprising the steps of:

adding energy to a sample of the fluid medium containing the granular material with the level of the energy set lower than the breakdown threshold energy level of the fluid medium and lower than the breakdown threshold energy level of the granular material; and analyzing characteristics of the granular material based on the detected plasma ions.

2. A method of analyzing a fluid medium containing a granular material as defined in claim 1, wherein the analyzing step comprises determining the size of the granular material based on the amount of detected ions.

3. A method of analyzing a fluid medium containing a granular material as defined in claim 1, wherein the analyzing step comprises determining the density of the granular material based on the amount of detected ions.

4. A method of analyzing a fluid medium containing a granular material as defined in claim 1, wherein
the analyzing step comprises determining the concentration of the granular material in the sample based on the mean value of the detected ions.

5. A method of analyzing a fluid medium containing a granular material, said method comprising the steps of:
adding energy to a sample of the fluid medium containing the granular material with the level of the energy set lower than the breakdown threshold energy level of the fluid medium and higher than the breakdown threshold energy level of the granular material;
detecting plasma ions resulting from breakdown of the granular material;
analyzing at least one characteristic of the granular material based on the detected plasma ions; and
further analyzing constituents of the granular material by detecting light emission spectrums generated from the granular material when breakdown of the granular material occurs.

6. A method of analyzing a fluid medium containing a granular material as defined in claim 1 or 5, wherein
the energy is added by activating a laser from a laser generating means, and controlling the laser to have an energy level lower than the breakdown threshold energy level of the fluid medium and higher than the breakdown threshold energy level of the granular material.

7. A method of analyzing a fluid medium containing a granular material as defined in claim 6, wherein
the laser is activated in a series of pulses.

8. A method of analyzing a granular material as defined in claim 7, wherein
the wavelength of the laser is set to be outside the range of the light emission spectrums which are generated when the breakdown of the granular material occurs.

9. A method of analyzing a granular material as defined in claim 5, wherein
the fluid medium is a liquid and the granular material breakdown energy level is lower than the breakdown threshold energy level of bubbles generated in the sample.

10. An apparatus for analyzing a fluid medium containing a granular material comprising:
a cell for holding a sample of the fluid medium containing the granular material;
means for irradiating a laser onto the sample with an energy level lower than the breakdown threshold energy level of the fluid medium and higher than the breakdown threshold energy level of the granular material;
a pair of positive and negative electrodes disposed on either side of the sample;
means for detecting plasma ions resulting from breakdown of the granular material; and
means for analyzing characteristics of the granular material based on the detected plasma ions.

11. An apparatus for analyzing a fluid medium containing a granular material comprising:
a cell for holding a sample of the fluid medium containing the granular material;
means for irradiating a laser onto the sample with an energy level lower than the breakdown threshold energy level of the fluid medium and higher than the breakdown threshold energy level of the granular material;
a pair of positive and negative electrodes disposed on either side of the sample;
means for detecting plasma ions resulting from breakdown of the granular;
means for analyzing characteristics of the granular material based on the detected plasma ions; and
means for further analyzing constituents of the granular material by detecting light emission spectrums generated upon breakdown of the granular material.

12. An apparatus for analyzing a fluid medium containing a granular material as defined in claim 10 or 11, further comprising:
means for automatically changing the sample in the cell; and wherein
said irradiating means irradiates the laser onto the granular material when the sample is changed.

13. An apparatus for analyzing water for detection of granular material therein, comprising:
a cell for receiving a sample of the water;
means for irradiating a laser onto the sample with an energy level lower than the breakdown threshold energy level of the water and of bubbles in the water and higher than the breakdown threshold energy level of the granular material;
a pair of positive and negative electrodes disposed on either side of the sample;
means for detecting plasma ions resulting from breakdown of the granular material;
means for analyzing characteristics of the granular material based on the detected plasma ions; and
means responsive to said analyzing means indicating inferior water for producing a warning signal and for stopping the supply of water from said apparatus to a using point.

14. A method of analyzing a fluid medium containing a granular material as defined in claim 1 or 5, wherein the plasma ions are detected by using a pair of positive and negative electrodes disposed on both sides of the sample.

15. A method of analyzing a fluid medium containing a granular material as defined in claim 5, wherein the characteristic is the size of the granular material.

16. A method of analyzing a fluid medium containing a granular material as defined in claim 5, wherein the characteristic is the numerical density of the granular material.

17. A method of analyzing a fluid medium containing a granular material as defined in claim 5, wherein the characteristic is the concentration of the granular material.

18. An apparatus for analyzing water for detection of granular material therein as defined in claim 13, further comprising an ultra-pure water producing apparatus including a plurality of components for supplying water to said cell.

19. An apparatus for analyzing water for detection of granular material therein as defined in claim 18, further comprising:
means for further analyzing constituents of the granular material by detecting light emission spectrums generated upon breakdown of the granular material; and
means for displaying identification of the component generating the granular material.

* * * * *